United States Patent [19]

Ludwig

[11] Patent Number: 4,640,119
[45] Date of Patent: Feb. 3, 1987

[54] UTILITY POLE TESTER
[75] Inventor: Frank Ludwig, Richmond, Mich.
[73] Assignees: P.T.E. Inc.; American Energy Services, Inc., both of Richmond, Mich.
[21] Appl. No.: 752,130
[22] Filed: Jul. 5, 1985
[51] Int. Cl.⁴ ............................................. G01N 3/30
[52] U.S. Cl. .......................................... 73/12; 73/82; 173/119
[58] Field of Search ............................. 73/12, 82, 839; 173/119, 120

[56] References Cited
U.S. PATENT DOCUMENTS

| | | | |
|---|---|---|---|
| 1,581,839 | 4/1926 | Dahlqvist | 73/82 |
| 1,708,262 | 4/1929 | Davis | 73/82 |
| 2,233,403 | 3/1941 | Dickinson et al. | |
| 2,389,030 | 11/1945 | Dana | |
| 2,522,544 | 9/1950 | Seyboth | |
| 3,385,105 | 5/1968 | Smith | 73/81 X |
| 3,494,431 | 2/1970 | Yoho et al. | 173/119 |
| 3,693,418 | 9/1972 | Kaspareck et al. | |
| 3,732,725 | 5/1973 | Allen, Jr. et al. | |
| 3,972,222 | 8/1976 | Yonkers et al. | |
| 4,034,603 | 7/1977 | Leeb et al. | |
| 4,182,163 | 1/1980 | Hoffmeyer | 73/82 |
| 4,236,402 | 12/1980 | McGuire | |
| 4,249,414 | 2/1981 | Barth | |
| 4,343,179 | 8/1982 | Astrom et al. | |
| 4,470,293 | 9/1984 | Redmon | |

FOREIGN PATENT DOCUMENTS 0515054 9/1976 U.S.S.R. ................................. 73/12

Primary Examiner—Charles A. Ruehl
Attorney, Agent, or Firm—Harness, Dickey & Pierce

[57] ABSTRACT

An apparatus for testing the strength of the sidewalls of hollow tubular members such as for example metal utility poles is disclosed. The present invention provides a self-contained mechanically actuated testing device which is operable to subject a pole to be tested to a concentrated impact force of a predetermined magnitude, the magnitude being selected such that the impacting portion of the tool will penetrate the sidewall if the strength thereof has diminished below an acceptable level.

12 Claims, 10 Drawing Figures

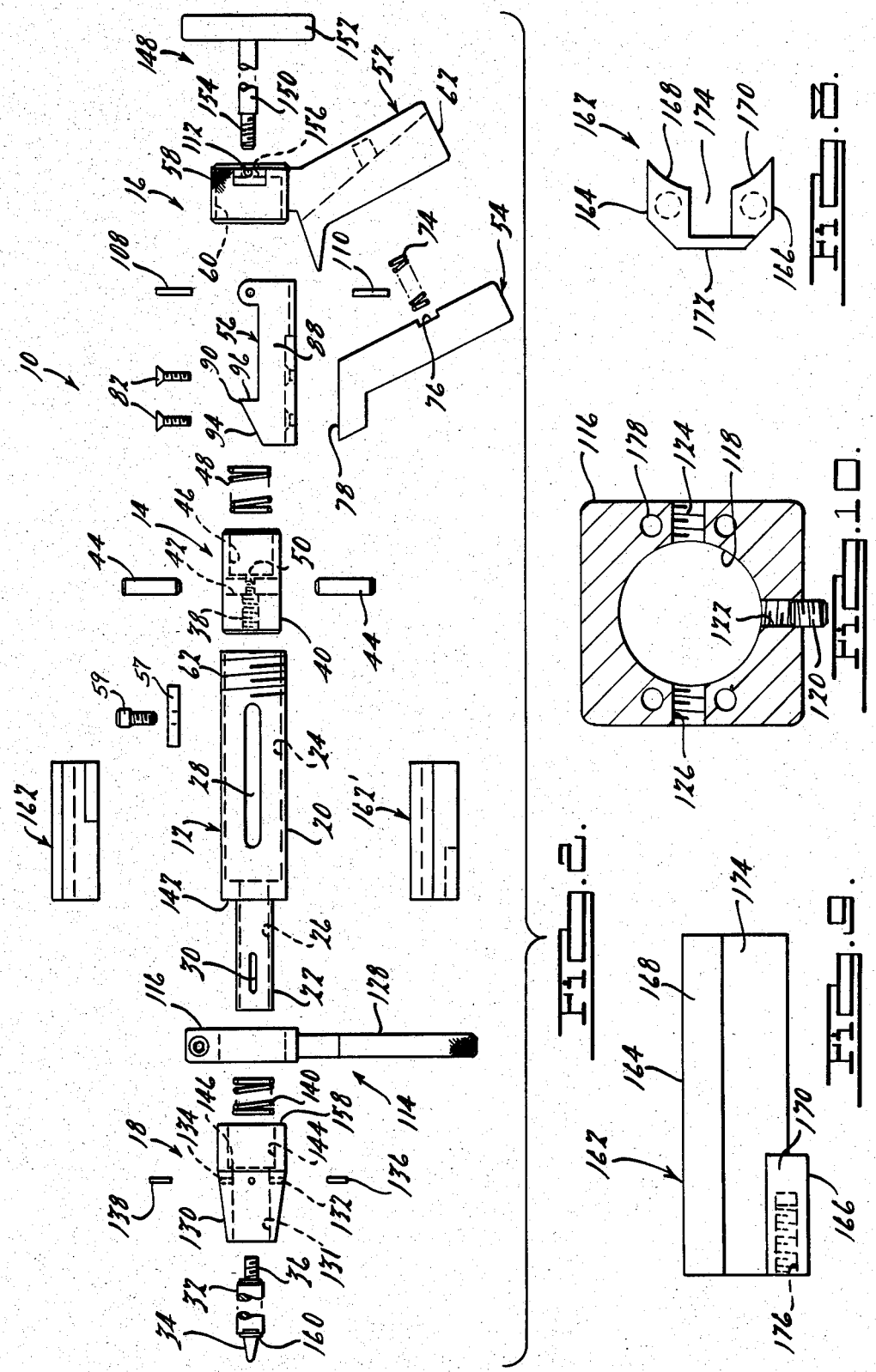

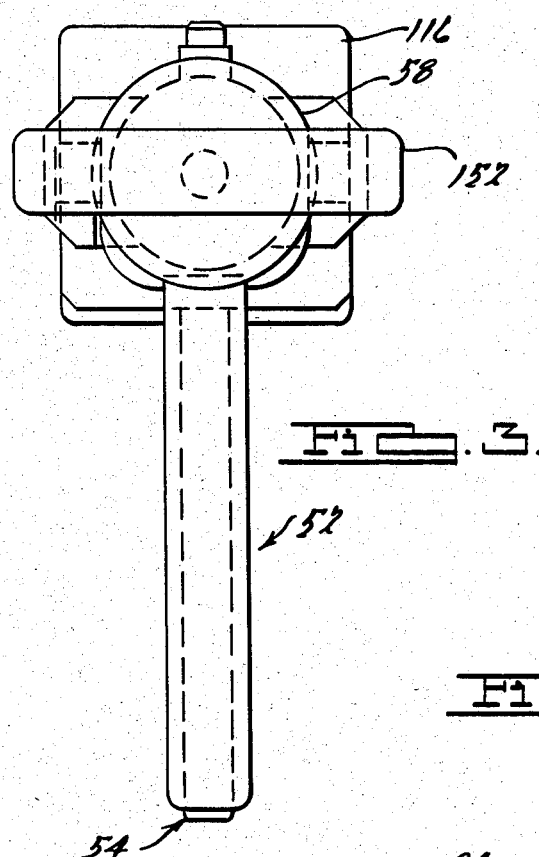
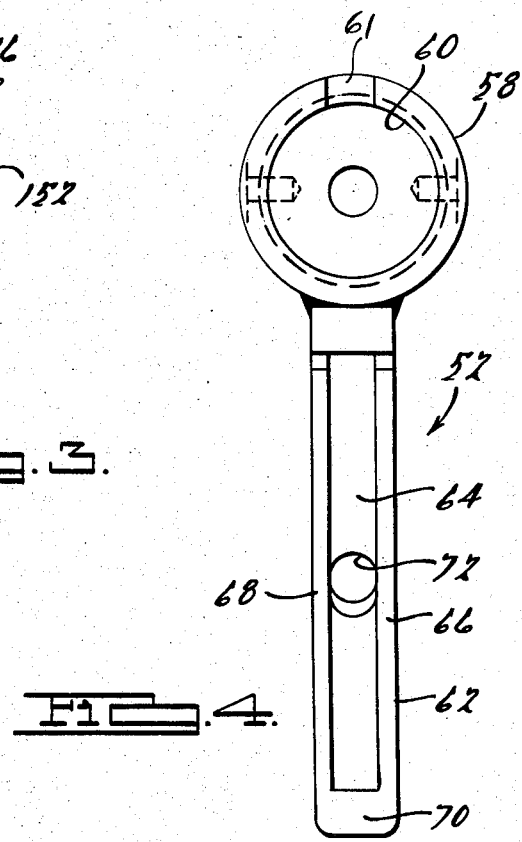
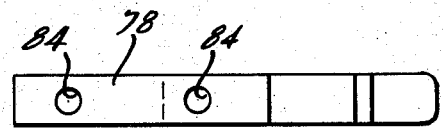
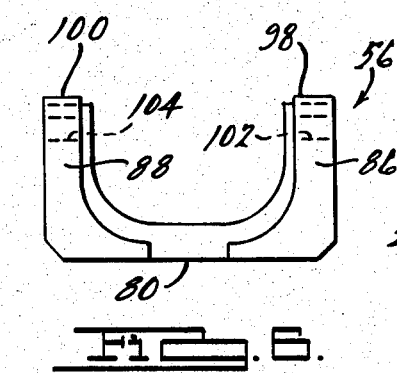
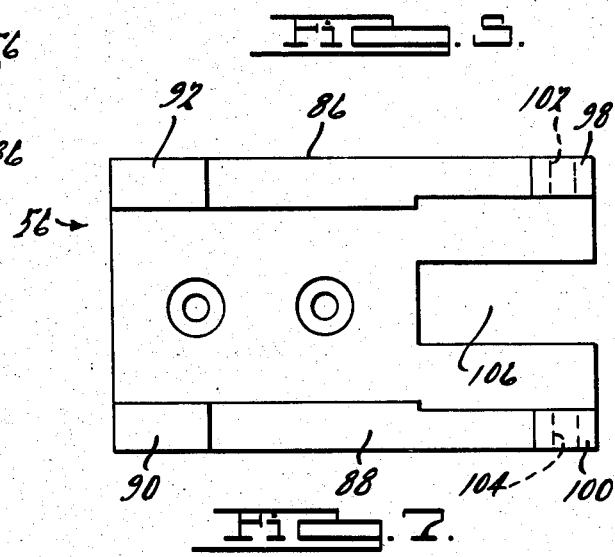

UTILITY POLE TESTER

BACKGROUND AND SUMMARY OF THE INVENTION

The present invention relates generally to utility pole testing apparatus and more particularly to such apparatus which is specifically designed to test the soundness of metal or steel poles utilized by various public utilities for supporting street lights and the like.

There exist a wide variety of applications wherein elongated steel or metal poles are utilized to support cables and/or street lights or the like in elevated relationship to ground level. Typically these metal poles comprise elongated tapered hollow tubes having a generally square or rectangular mounting plate fixedly secured to the lower end thereof such as by welding. The metal plate is designed to be bolted or otherwise secured to a suitable mounting pad such as a concrete pad having suitable threaded members embedded therein. While these poles are typically well treated by various means to retard the corrosive action of the elements when manufactured, nevertheless many of these poles have been in use under extreme adverse environmental conditions for extended periods of time and hence the corrosive inhibitors have degraded to the point where such poles have become subject to corrosion. Most commonly this corrosion is initiated in the interior of the pole where moisture becomes trapped and is able to act on the exposed metal surfaces therein. Once this corrosion begins it is only a period of time before the pole becomes sufficiently weakened to the point where it is no longer able to support its intended load. Accordingly, various users of such poles have become increasingly concerned with detecting such poles which have suffered excessive deterioration in order to replace same before they create a dangerous condition.

While various types of apparatus have been developed in an effort to provide suitable means whereby this interior corrosion may be efficiently and easily detected, none of the apparatus thus far developed have proved to be totally satisfactory. Because such poles are often located in locations not easily accessible, it is particularly desirable that any such testing equipment be easily portable. Further, it is of critical importance that the testing apparatus be particularly well designed to provide repeatable accurate and positive indications of the soundness of such metal poles without significant reliance on operator interpretation of the test results so as to avoid the possibility of both excessively corroded poles not being replaced as well as replacement of poles still having a sufficiently long service life remaining. Also, it should be noted that such testing apparatus will typically be utilized by relatively unskilled personnel and may be subject to a less than desirable degree of care both in use and in transportation. Accordingly, such apparatus should be ruggedly constructed and relatively simple and easy to use.

The present apparatus accomplishes these objectives by providing a relatively simple, straightforward testing apparatus which may be easily utilized by any individual without requiring excessive training in the operation thereof. Further, because the testing apparatus of the present invention incorporates a relatively few number of parts and is simple and straightforward in its construction, it is well suited to provide consistent and repeatable indications of the soundness of such poles.

The apparatus of the present invention incorporates a spring loaded piston having affixed to a forward end thereof a plunger having a suitable contoured conical forward end member which is designed to impact the outer surface of a metal utility pole. The spring loaded plunger is designed to be manually retracted into a cocked position whereupon the apparatus may be pressed against a pole to be tested and a trigger meachanism actuated thereby releasing the piston and plunger causing the conical projection to impact the outer surface of the pole. If the pole has suffered excessive corrosion to the extent where the wall thickness has deteriorated sufficiently to allow the conical projection to penetrate therethrough, the pole will be deemed to be unsafe and may thus be scheduled for replacement. If, however, the projection does not penetrate the surface at all or sufficiently, this will provide an indication the pole is presently sufficiently sound to endure further usage.

The testing apparatus of the present invention is not designed to provide an indication of the absolute strength of the wall of the pole being tested but rather is designed to provide an indication whether the wall thickness possesses a strength in excess of a predetermined minimum such that the utility pole will not create a hazard within a predetermined future time period and is therefore suitable for further use. The specific force required in order to cause the conical projection to penetrate any given wall thickness of such poles may be easily controlled by coordinating the driving spring strength in conjunction with the contour of the conical projection which impacts the pole surface. Thus the present invention is well suited for testing of a wide variety of poles and may be easily adjusted to provide an indication of whether the strength of the pole is above or below any desired predetermined level by merely altering the strength of the driving spring member or alternatively altering the contour of the impacting conical projection. Further, because the testing apparatus of the present invention incorporates a relatively few number of parts, it is relatively inexpensive to manufacture yet is able to offer a high degree of reliability both in terms of operation as well as in terms of consistency between successive tests. Also, even in the event that a portion thereof may suffer a failure, the simple nature of the testing apparatus enables a relatively quick and easy repair to be effected.

Additional advantages and features of the present invention will become apparent from the subsequent description and the appended claims taken in conjunction with accompanying drawings.

BRIEF DESCRIPTION OF THE DRAWINGS

FIG. 2 is an exploded elevational view of the testing apparatus shown in FIG. 1 with portions thereof rotated 90° for illustration purposes;

FIG. 3 is an end view of the testing apparatus illustrated in FIG. 1;

FIG. 4 is an end view of the handle member forming a part of the testing apparatus illustrated in FIG. 1;

FIG. 5 is a plan view of the trigger member forming a part of the testing apparatus illustrated in FIG. 1;

FIG. 6 is an end view of the trigger release member;

FIG. 7 is a plan view of the release member illustrated in FIG. 6;

FIGS. 8 and 9 are end and side views respectively of a guard member forming a part of the testing apparatus illustrated in FIG. 1; and FIG. 10 is a section view of a block member forming a portion of the auxiliary handle illustrated in FIG. 2.

DESCRIPTION OF THE PREFERRED EMBODIMENT

Figure 1:
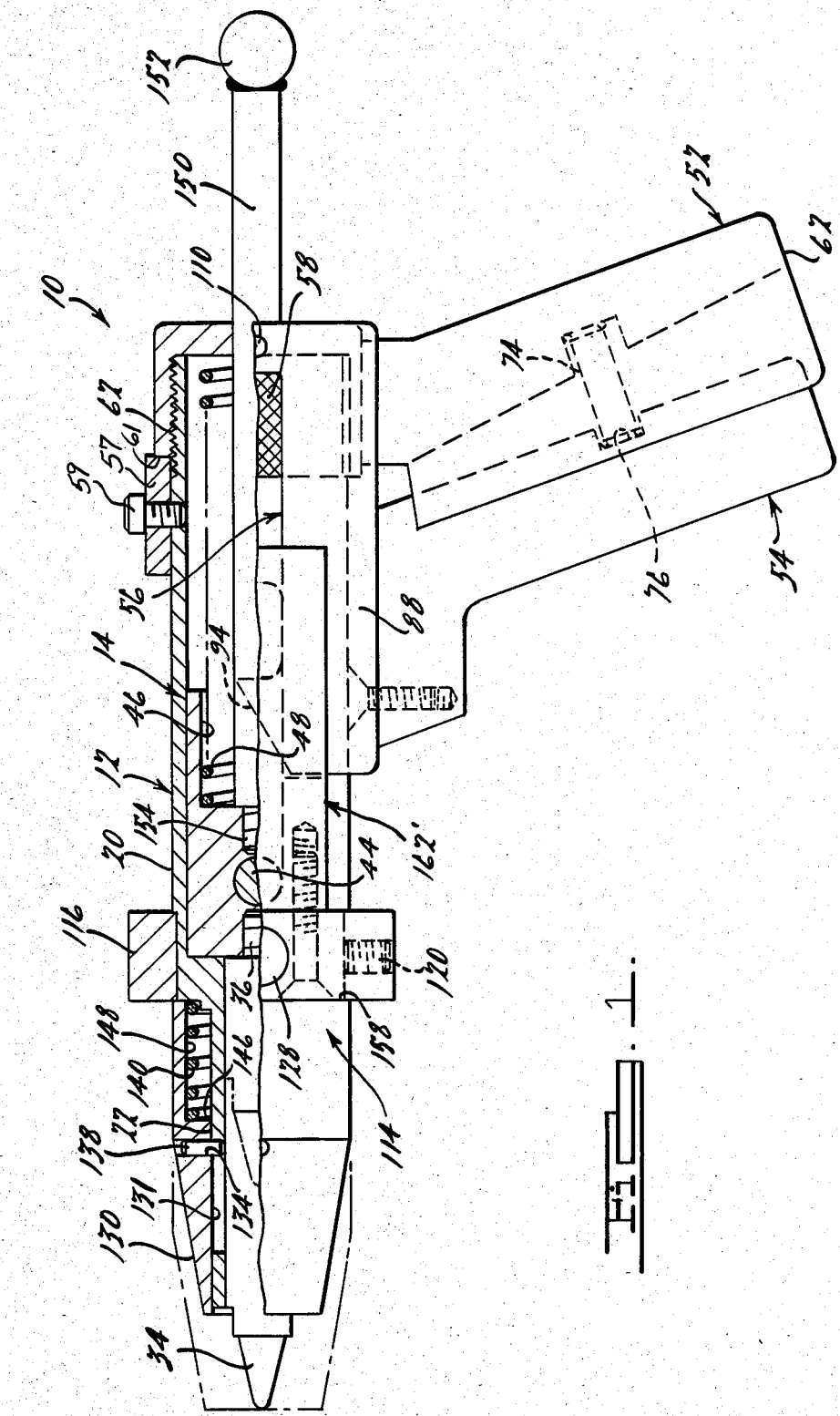
FIG. 1 is an elevational view of the testing apparatus in accordance with the present invention, portions thereof being shown in section.

Referring now to the drawings and in particular to FIGS. 1 and 2, there is illustrated a pole testing apparatus in accordance with the present invention being indicated generally at 10. Pole testing apparatus 10 comprises a generally cylindrically shaped elongated hollow housing 12 within which is disposed a plunger assembly 14 which is designed to be reciprocably moveable therein. A trigger assembly 16 is also provided being secured to one end of the housing and is designed to cooperate with the plunger assembly 14 in order to retain it in a cocked position until such time as the test is desired to be performed. A protective nose assembly 18 is also movably secured to the opposite end of the housing 12 and is designed to surround and protect an outwardly projecting portion of the plunger assembly 14 so as to protect same from damage.

Housing 12, as previously mentioned, comprises an elongated generally cylindrically shaped main body portion 20 and an integrally formed reduced diameter generally cylindrically shaped portion 22 extending axially outwardly from one end of main body portion 20. The main body portion 20 has a relatively large diameter bore 24 extending therethrough which opens into a coaxially positioned reduced diameter bore 26 extending outwardly through cylindrical portion 22. A pair of substantially identical coextensive axially elongated slots 28 are provided being positioned in diametrically opposed relationship to each other and intermediate the ends of the main body portion 20 of the housing 12 and similarly a pair of substantially identical coextensive axially elongated diametrically opposed slots 30 are provided in the reduced diameter cylindrically shaped portion 22 intermediate the ends thereof.

The plunger assembly 14 comprises a generally cylindrically shaped elongated plunger member 32 having an axially outwardly projecting concentrically positioned generally conically shaped nose portion 34 provided at one end thereof and a threaded reduced diameter shank portion 36 extending outwardly from the opposite end thereof. Threaded portion 36 is designed to be received within a threaded bore 38 provided in the forward end of a generally cylindrically shaped elongated piston member 40 which is designed to be movably disposed within the relatively large diameter bore 24 provided in the main body portion 20 of the housing 12. Piston member 40 also includes a bore 42 extending diametrically therethrough approximately midway along the length thereof. A pair of relatively short pin members 44 are designed to be received within this bore 42 and to project generally radially outwardly therefrom in opposite directions. Preferably pin members 44 will be sized relative to the diameter of bore 42 to provide a friction fit therein although alternatively they may be secured therein an any other suitable manner such as by threading same or the like. A relatively large diameter bore 46 extends axially inwardly from the opposite end of piston member and is designed to provide a seat within which a suitable coil spring member 48 may be positioned. A relatively small diameter threaded bore 50 is also provided being positioned coaxially with respect to and forms a continuation of relatively large diameter bore 46 and opens into the threaded bore 38 which is adapted to receive the threaded portion 36 of plunger member 32.

Trigger assembly 16 comprises a handle member 52, a trigger member 54, and a hook member 56. As best seen with reference to FIGS. 2 and 4, handle member 52 comprises a generally cylindrically shaped knurled upper cap portion 58 having a threaded bore 60 extending inwardly from one end thereof which is adapted to threadedly engage the threaded end portion 62 provided on main body portion 20 of the housing member 12. Secured to and depending from this cylindrical portion 58 is a relatively thin angularly positioned hand grip portion 62 which is fixedly attached thereto in a suitable manner such as by welding or the like. As shown in FIG. 4, the hand grip portion 62 includes a generally elongated rectangularly shaped cavity 64 defined by laterally spaced elongated flange portions 66 and 68 and a lower interconnecting flange portion 70. A relatively small diameter shallow bore 72 is provided within this cavity 64 extending into the hand grip portion and is designed to receive a suitable coil spring 74 therein.

Trigger member 54 comprises a generally irregularly shaped elongated member generally as shown in FIGS. 2 and 5 which has a thickness which is designed to enable it to be movably received in part within the cavity 64 provided on the hand grip portion 62 of the handle member 52. A notch 76 is also provided intermediate the length of trigger member 54 against which the opposite end of coil spring member 74 is designed to act. Trigger member 54 has a generally planar upper surface 78 which is designed to be secured to a generally planar lower surface 80 of hook member 56 by means of a pair of suitable threaded fasteners 82 which are received within a pair of spaced tapped bores 84 provided in surface 78 thereof.

As best seen with reference to FIGS. 6 and 7, hook member 56 is generally U-shaped in cross section and includes a pair of longitudinally extending upwardly (as shown) projecting substantially parallel spaced flange members 86, 88, each of which has a substantially identical upwardly extending projection 90, 92 at the forward end thereof each of which is defined by a generally inclined ramp surface 94 and a generally vertically (as shown) oriented trailing surface 96. A pair of generally upwardly extending projections 98, 100 are also provided at the opposite end of each of flange portions 86, 88 which is designed to accommodate coaxially positioned bores 102, 104 extending therethrough. As shown in FIG. 7, a relatively wide longitudinally extending notch 106 is provided in the lower portion of hook shaped member 56 so as to enable the hook shaped member 56 to straddle the hand grip portion 62 of the handle member 52. A pair of pin members 108, 110 are provided which are designed to extend through bors 102, 104 provided in each of the upstanding projections 98, 100 provided on hook members 56 and are received within suitable sized diametrically positioned bores 112 provided adjacent the rear surface of cap member 58 so as to pivotably connect hook member 56 thereto.

In order to assemble the testing apparatus of the present invention, the threaded shank portion 36 of the plunger member 32 is first threaded into the bore 38 provided in the forward end of the piston member 40.

Thereafter, the piston member 40 is inserted into the enlarged diameter bore provided in the main body portion 20 of housing 12 after which pin members 44 may be inserted through respectively diametrically opposed slots 28 provided in main body portion 20 of housing 12 and into the diametrically extending bore 42 provided in the piston member 40. Thereafter, the spring member 48 is seated within the relatively large bore 46 provided on the back side of the piston member 40 after which the cap portion 58 of handle member 52 is threaded onto the main body portion 20 of the housing 12. A relative short block 57 is provided which is designed to be secured to housing 12 by means of a fastener 59 with a portion thereof projecting into a recess 61 in cap portion 58 so as to prevent relative rotation between cap member 58 and housing 12. Next, the hook member 56 is secured to the trigger member 54 by means of threaded fasteners 82 after which the thus formed assembly is fitted onto the handle member and respective pin members 108, 110 inserted through openings 102 and 104 into the cap portion 58 of the handle member 52. Simultaneously therewith spring memer 74 is positioned so as to extend between the notch 76 provided on the trigger member 54 and the bore 72 provided within the channel 64 on the hand grip portion 62.

In order to facilitate use of the testing apparatus 10 of the present invention, an auxiliary handle assembly 114 is also provided which comprises a generally rectangularly shaped block 116 having a bore 118 extending therethrough of a diameter approximately equal to the diameter of the main body portion 20 of the housing 12. A suitable set screw 120 is provided within a threaded bore 122 in block member 116 which is adapted to be moved into engagement with main body portion 20 of the housing 12 subsequent to assembly of the block member 116 thereto so as to exert a clamping force to lock the block member 116 in position thereon. Block member 116 also includes a pair of diametrically extending threaded openings 124, 126 extending inward from laterally opposite sidewalls therof. These threaded openings 124, 126 are designate to accomodate a generally cylindrically shaped elongated auxiliary handle member 128 which may be easily threaded into one or the other of these threaded openings so as to accommodate either right or left handed operators.

A protective nose assembly 18 is also provided which includes a cone member 130 designed to surround the outwardly projecting conical portion 34 of the plunger member 32 and is telescopically movably fitted to the forwardly projecting cylindrical portion 22 of the housing 12 which is movably received within axially extending bore 131 extending therethrough. Nose cone 130 includes a pair of diametrically extending bores 132, 134 provided therein each of which is adapted to receive a pin member 136, 138 which is intended to extend into engagement with respective dimetrically opposed slots 30 provided on the reduced diameter cylindrical portion 22 of the housing 12. A spring member 140 is also provided extending between the shoulder 142 provided on the housing member 12 into an axially extending bore 144 provided in cone member 130 and bearing against a stepped portion 146 provided therein. Spring 140 operates to bias the cone 130 into an axially forward position wherein it is positioned in surrounding protecting relationship to the outwardly projecting pluner member 32.

A cocking handle member 148 is also provided which comprises an elongated rod member 150 having a T-handle 152 secured to one end thereof and the other end of which is provided with a threaded portion 154. Threaded portion 154 is designed to be inserted through an opening 156 provided in the axially outer or rearward end of cap member 58 and coaxially through spring member 48 and threaded into relatively small diameter bore 50 provided in the piston member 40.

Thus in order to utilize the testing apparatus of the present invention, an operator will initially cock the testing apparatus by grasping T-handle 148 and pulling axially outwardly thereon so as to move piston 40 and associated plunger member 32 rearwardly with respect to the housing 12. As piston member 40 is moved rearwardly, outwardly projecting pin members 44 will move longitudinally alon respective slots 28 provided in the housing 12 until such time as they engage the forward beveled edge or ramp surface 94 of respective projections 90 and 92 provided on hook member 56. As these pin members 44 continue to move axially rearwardly under the pulling force exerted by the handle member 148, they will cause the hook member 56 to be pivoted downwardly (as viewed in FIG. 1) until such time as the pin members 44 have moved beyond the apex of the projections 90 and 92 at which time spring member 74 acting against the trigger member 54 will cause the hook member 56 to pivot back upwardly into its at rest position. At this time, the pulling pressure on the T-handle 148 may be released and the pin members 44 will engage the flat surface area 96 lying axially rearwardly of the inclined ramp surface 94 of hook member 56 thus retaining piston 40 and associated plunger 32 in a cocked position with spring member 48 being in a compressed condition. Next, the protective cone member 130 of the testing apparatus will be pressed against a portion of a utility pole to be tested with sufficient force as to overcome the biasing action of spring member 140 thereby causing the cone member 130 to be moved axially rearwardly with respect to the housing 12. Because the plunger 32 and piston 40 are in a cocked position, the conical portion 34 of the plunger member 32 will be disposed within the reduced diameter cylindrical portion 22 of the housing 12 thus enabling the protective nose cone 130 to be moved axially rearwardly until such time as the rear surface 158 thereof engages the axially facing shoulder 142 of the main body portion 20 of the housing 12.

While the testing apparatus is thus held in position against the pole to be tested, the trigger member 54 is moved reardwardly by the operator thereby causing the hook member 56 to pivot downwardly releasing the pin members 44 therefrom whereby the spring member 48 is operative to drive the piston 40 and associated plunger member 32 axially forwardly thereby causing conical portion 34 to impact the outer surface of the pole member. If the resulting impact force is sufficient to cause penetration of the conical portion 34 of the plunger member 32 into or through the sidewall of the pole member, it is clear that the pole member has suffered sufficient corrosion as to require replacement. Alternatively, however, if the conical portion of the plunger member does not penetrate the wall of the utility pole, this provides an indication that the pole still retains sufficient strength to be maintained in service for an additional period of time. The degree of force with which the conical portion 34 of the plunger member 32 impacts the pole member may be easily controlled and calibrated by proper selection of both the contour of the conical portion 34 of the plunger member as well as the strength of the spring member 48. Thus, it is possible to provide different combinations of springs and/or plunger members which are specifically calibrated for use in testing different diameter and height pole members so as to provide a positive go/no go indication of the soundness thereof. It should be noted that plunger member has been illustrated and described with a conically shaped impacting portion so as to facilitate removal thereof from the pole in the event it penetrates the wall thereof, however, other shapes may be utilized therefor as desired. However, in order to limit the degree of penetration, it is preferable to provide an annular shoulder 160 surrounding the impacting conical portion.

Guard means are also provided which are secured to the block member forming a portion of the auxiliary handle and are designed to overlie the axially elongated slots 28 provided in the main body portion 20 of the housing 12 so as to prevent entry of foreign articles which may interfere with the rapid forward movement of the piston member 40 so as to thereby create the potential for an inaccurate test result occuring. The guard means comprise two guard members which are substantially mirror images of each other and hence only a single member will be described in detail. As best seen with reference to FIGS. 8 and 9, guard member 162 includes a pair of leg members 164, 166 each having generally arcuately shaped outwardly projecting end surfaces 168, 170 designed to mate with cylindrical contour of the main body portion 20 of the housing 12. Each of these leg members 164, 166 is interconnected by a flange portion 172 extending therebetween and integrally formed therewith so as to define an axially elongated cavity 174 within which the radially outwardly projecting pin members 44 may be free to move. As shown in FIG. 9, leg portion 166 extends only a short distance along the length of guard member 162 and hence the remaining length of the guard is open along the lower edge into cavity 174 so as to accommodate movement of hook member 56 with respect thereto. Suitable threaded openings 176 are provided in each of the leg members which are designed to receive bolt members extending through respective openings 178 provided on the block members 116 forming a portion of the auxiliary handle asembly in order to secure guard members 162 in position on testing apparatus 10.

Accordingly, as may now be appreciated, the testing apparatus of the present invention provides a relatively simple and straightforward completely portable mechanically actuated testing tool which is easily operated by an individual and is able to provide repetitive and accurate indication of the soundness of virtually any metal utility pole.

While it will be apparent that the preferred embodiment of the invention disclosed is well calculated to provide the advantages and features above stated, it will be appreciated that the invention is susceptible to modification, variation and change without departing from the proper scope or fair meaning of the subjoined claims.

I claim:

1. A portable testing apparatus for determining the degree of degradation of metal surface, said testing apparatus comprising:
    an elongated housing having a bore extending longitudinally therethrough;
    removable closure means closing one end of said bore;
    piston means movably disposed within said bore, said piston means including an impacting portion removably secured to said piston means and movable into and out of said housing, said impacting portion being operative to impact said metal surface to be tested;
    biasing means operative to urge said piston means in a forward direction whereby said impacting portion extends outwardly of said housing;
    handle means secured to said housing, said handle means including trigger means operative when in a first position to retain said piston means in a rearward position within said housing and when moved to a second position to release said piston whereby said biasing means may operate to drive said piston forwardly with respect to said housing so as to cause said impacting portion to impact said metal surface with a predetermined force.
    a nose cone assembly longitudinally movably secured to said housing, said nose cone assembly being operative to surround and protect a part of said impacting portion projecting outwardly of said housing when said pisotn is in a forward position.

2. A testing apparatus as set forth in claim 1 wherein said nose cone assembly is movable to a rearwardly disposed position in response to movement thereof into engagement with said metal surface.

3. A testing apparatus as set forth in claim 1 wherein said biasing means and the surface part of said impacting portion which is engageable with said metal surface are selected such that said metal surface is subjected to a predetermined force and the ability of said surface to resist penetration of said surface part is indicative of a predetermined minimum strength of said surface.

4. A testing apparatus as set forth in claim 1 wherein said testing apparatus is fully self-contained.

5. A testing apparatus as set forth in claim 1 wherein said piston means includes a pair of diametrically outwardly extending pin members and said trigger means includes a pair of spaced lever arms engageable with said pin members to retain said piston means in a rearward position.

6. A testing apparatus as set forth in claim 5 wherein said trigger means is pivotably secured to said removable closure means.

7. A testing apparatus as set forth in claim 6 further comprising biasing means acting between said handle means and said trigger means to bias said trigger means into said first portion.

8. A testing apparatus as set forth in claim 5 wherein said hosuing includes a pair of diametrically spaced longitudinally extending slots, said pin members projecting generally radially outwardly of said housing through said slots.

9. A testing apparatus as set forth in claim 5 further comprising elongated guard overlying said pin members and operative to allow longitudinal movement thereof.

10. A testing apparatus as set forth in claim 1 wherein said testing apparatus further comprises second handle means secured to said housing adjacent a forward end thereof, said second handle means being operative to aid in maintaining said testing apparatus in position with respect to said metal surface.

11. A testing apparatus as set forth in claim 1 wherein said nose cone assembly further includes a pair of diametrically spaced radially inwardly extending pin members, said pin members being longitudinally movably received within longitudinally elongated slots provided in a forward portion of said housing so as to limit longitudinal movement of said nose cone assembly with respect thereto.

12. A testing apparatus as set forth in claim 1 further comprising locking means operative to mechanically lock said removable closure means in a desired circumferential orientation with respect to said housing.

* * * * *